(12) United States Patent
Motzer et al.

(10) Patent No.: US 7,848,894 B2
(45) Date of Patent: Dec. 7, 2010

(54) NON-DESTRUCTIVE INSPECTION APPARATUS

(75) Inventors: William P. Motzer, Seattle, WA (US); Gary E. Georgeson, Federal Way, WA (US)

(73) Assignee: The Boeing Company, Chicago, IL (US)

( * ) Notice: Subject to any disclaimer, the term of this patent is extended or adjusted under 35 U.S.C. 154(b) by 60 days.

(21) Appl. No.: 12/400,244

(22) Filed: Mar. 9, 2009

(65) Prior Publication Data

US 2010/0228506 A1   Sep. 9, 2010

(51) Int. Cl.
*G01B 5/28* (2006.01)
(52) U.S. Cl. .................... 702/35; 73/602; 73/866.5; 702/150
(58) Field of Classification Search .......... 702/42, 702/127, 141, 150, 152, 156, 160, 35, 36, 702/38, 39; 73/602, 620, 625, 641; 340/692; 356/398, 431; 701/29

See application file for complete search history.

(56) References Cited

U.S. PATENT DOCUMENTS 6,023,986 A * 2/2000 Smith et al. ............. 73/866.5
2008/0245150 A1* 10/2008 Katayama et al. ........... 73/602

OTHER PUBLICATIONS

Gieske, J.H., "Evaluation of scanners for C-scan imaging for nondestructive inspection of aircraft", vol. 2, No. 11, pp. 1-12, (1997).
Analog Devices, "High precision tri-axis inertial sensor", pp. 1-5, (2007).
Yazdi, N., et al., "Micromachined inertial sensors", vol. 86, No. 8, pp. 1640-1659, (1998).

* cited by examiner

*Primary Examiner*—John H Le
(74) *Attorney, Agent, or Firm*—Klintworth & Rozenblat IP LLC

(57) ABSTRACT

A free-hand inspection apparatus for non-destructively inspecting a structure includes an array and an inertial sensor. The array includes a plurality of elements for transmitting and receiving inspection signals towards and from a structure being inspected. The inertial sensor measures acceleration and angular rotation rate in X, Y, and Z directions of the array.

26 Claims, 4 Drawing Sheets

NON-DESTRUCTIVE INSPECTION APPARATUS

BACKGROUND OF THE DISCLOSURE

It is often necessary to non-destructively inspect a structure in order to determine inconsistencies in the structure. For instance, an in-service aircraft may be inspected during routine maintenance. One conventional method of inspecting such a structure is to use a portable X-Y scanner, such as the Boeing MAUS V, Pocket UT Rapiscan, or the Andscan, to produce C-scan images of ultrasonic or eddy current data of the structure being inspected. Most of these devices utilize a single element which must be scanned across the surface of the structure, which may take substantial time. The two-dimensional ultrasonic or eddy current scanning often requires expensive and sophisticated X-Y scanners or hand-held probes with indexed X-Y bridges or cantilever arms. Automated portable X-Y scanners that produce C-scan images may be complicated to operate, may need to be mounted to the surface of the structure being inspected, may take significant time to set up, and may be costly. Hand-held devices that use encoder wheels may take a significant amount of time, and may produce low quality images. Hand-held devices may produce better images with a mounted X-Y bridge. However, this may add to the complexity, and may also be time-consuming due to the amount of manual scanning required for even small areas. X-Y bridges may also be difficult to use upside down, for instance to inspect a wing of an in-service aircraft. X-Y bridges may also have problems inspecting structures with surfaces having complex curvatures.

A non-destructive inspection apparatus and/or method of use is needed which may solve one or more problems of one or more of the conventional non-destructive inspection apparatus and/or methods of use.

SUMMARY OF THE DISCLOSURE

In one aspect of the disclosure, a free-hand inspection apparatus may be provided for non-destructively inspecting a structure. The free-hand inspection apparatus may comprise an array and an inertial sensor. The array may comprise a plurality of elements for transmitting and receiving inspection signals towards and from a structure being inspected. The inertial sensor may be for measuring acceleration and angular rotation rate in X, Y, and Z directions of the array.

In another aspect of the disclosure, an inspection apparatus may be provided for non-destructively free-hand inspecting a structure. The inspection apparatus may comprise an inspection device, an array, an inertial sensor, and at least one computer. The inspection device may be for transmitting and receiving inspection signals. The array may comprise a plurality of elements for: receiving the inspection signals of the inspection device; transmitting the inspection signals received from the inspection device towards a structure being inspected; and for receiving the inspection signals back from the structure being inspected. The inertial sensor may be for measuring acceleration and angular rotation rate in X, Y, and Z directions of the array relative to a surface of the structure being inspected. The at least one computer may be used for: collecting and analyzing data from the array and the inertial sensor; determining velocities, positions, and orientations of the array relative to the surface of the structure based on the inertial sensor data; correlating the array data relative to the determined positions and orientations of the array; and outputting inspection results at multiple locations of the structure based on the correlated array data relative to the determined positions and orientations of the array.

In still another aspect of the disclosure, a method of non-destructively free-hand inspecting a structure may be provided. In one step, an inspection apparatus may be provided. The inspection apparatus may comprise an array comprising a plurality of elements, an inertial sensor, and at least one computer. In another step, the array may be moved over a surface of the structure. In an additional step, inspection signals may be transmitted and received, using the array, to and from the structure. In another step, acceleration and angular rotation rate data of the array in X, Y, and Z directions may be transmitted using the inertial sensor. In still another step, inspection data of the structure from the array and the acceleration and angular rotation rate data from the inertial sensor may be collected using the at least one computer. In an additional step, velocities, positions, and orientations of the array relative to the surface of the structure may be determined using the at least one computer based on the collected acceleration and angular rotation rate data from the inertial sensor. In another step, the collected inspection data of the structure may be correlated, using the at least one computer, with the determined positions and orientations of the array relative to the structure. In still another step, inspection results at each location of the surface of the structure over which the array was moved may be outputted using the at least one computer.

These and other features, aspects and advantages of the disclosure will become better understood with reference to the following drawings, description and claims.

DETAILED DESCRIPTION OF THE DISCLOSURE

The following detailed description is of the best currently contemplated modes of carrying out the disclosure. The description is not to be taken in a limiting sense, but is made merely for the purpose of illustrating the general principles of the disclosure, since the scope of the disclosure is best defined by the appended claims.

Figure 1:
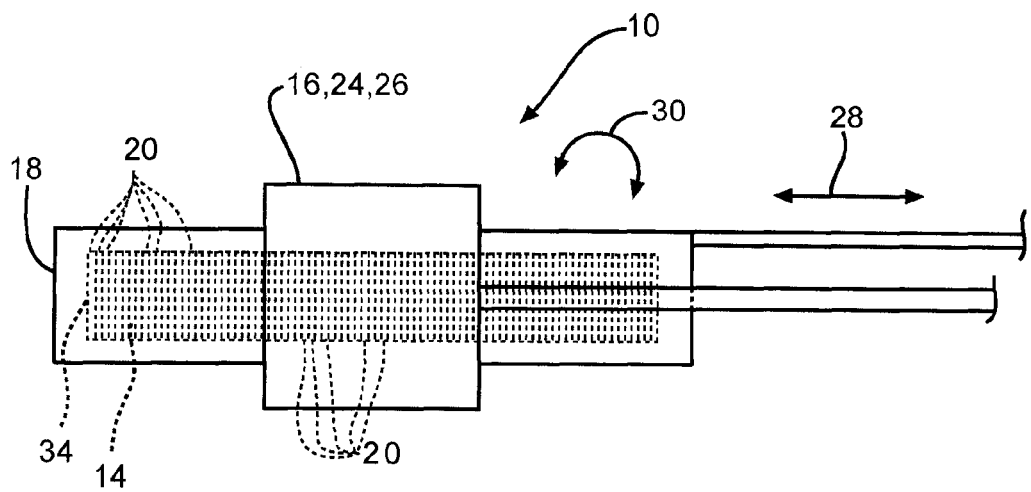
FIG. 1 illustrates a top view of one embodiment of a free-hand inspection apparatus which may be used for non-destructively inspecting a structure.
Figure 2:
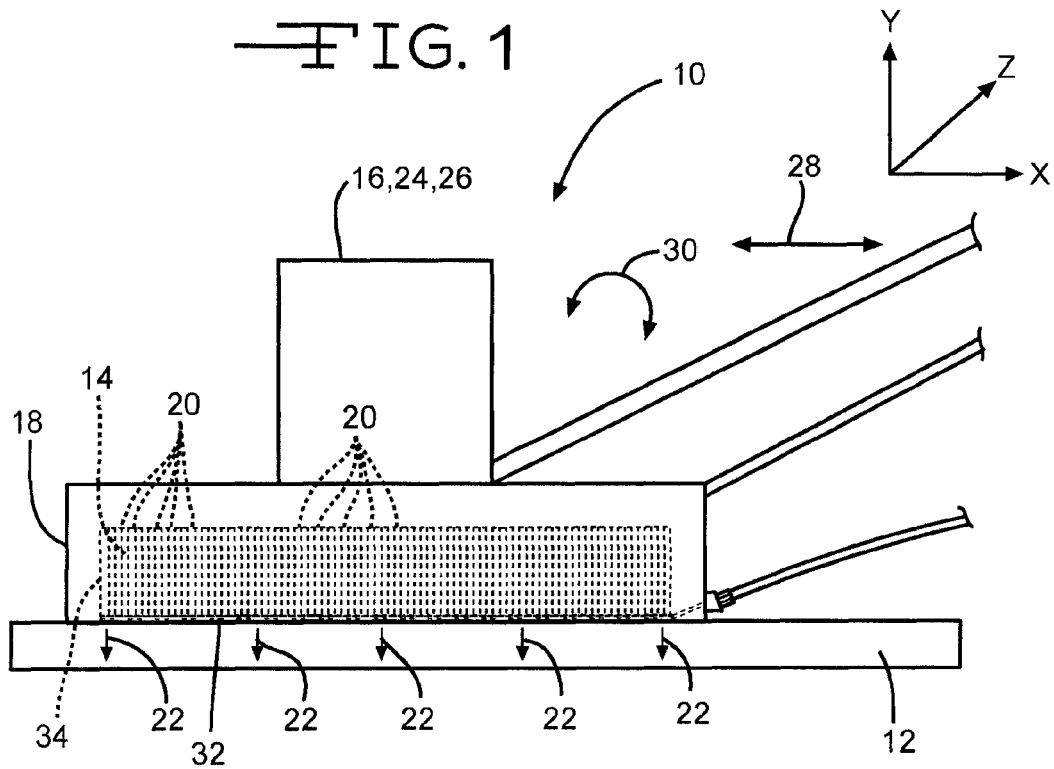
FIG. 2 illustrates a side view of the free-hand inspection apparatus of FIG. 1.
Figure 3:
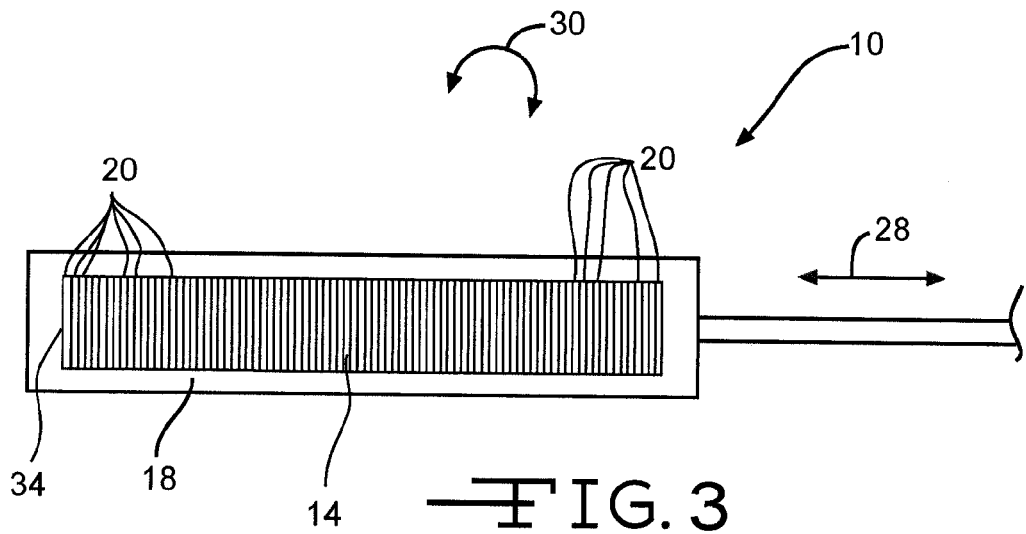
FIG. 3 illustrates a bottom view of the free-hand inspection apparatus of FIG. 1.

FIGS. 1, 2, and 3 illustrate, top, side, and bottom views of a free-hand inspection apparatus 10 which may be used for non-destructively inspecting a structure 12. The structure 12 may comprise an in-service aircraft, production aircraft, boat hull, automobile, pipe, building, bridge, or another type of structure that requires inspection. The structure 12 may comprise a linear structure, a three-dimensional curved structure, such as a partial cone or hemisphere, or other type of structure. As shown in FIGS. 1-3, the free-hand inspection apparatus 10 may comprise an array 14, an inertial sensor 16, and a bubble-shoe housing 18. The array 14 may comprise a plurality of elements 20 for transmitting and receiving inspection signals 22 towards and from the structure 12 being inspected. The array 14 may comprise a linear-array. The elements 20 may be adapted to transmit and receive inspection signals 22 comprising at least one of ultrasonic signals, eddy current signals, magnetic signals, and/or other types of inspection signals. The inertial sensor 16 may comprise a micro-electro-mechanical system inertial sensor (MEMS inertial sensor) comprising an accelerometer 24 and a rate gyroscope 26.

The inertial sensor 16 may be adapted to measure acceleration 28 and angular rotation rate 30 in X, Y, and Z directions of the array 14 using an array centered coordinate system. The bubble-shoe housing 18 may be attached to the array 14 and be adapted to supply couplant 32 to the surface of the structure 12 being inspected. The array 14 may be disposed within a cavity 34 of the bubble-shoe housing 18. The inertial sensor 16 may be attached to the bubble-shoe housing 18. In other embodiments, one or more components of the free-hand inspection apparatus 10 may vary.

Figure 4:
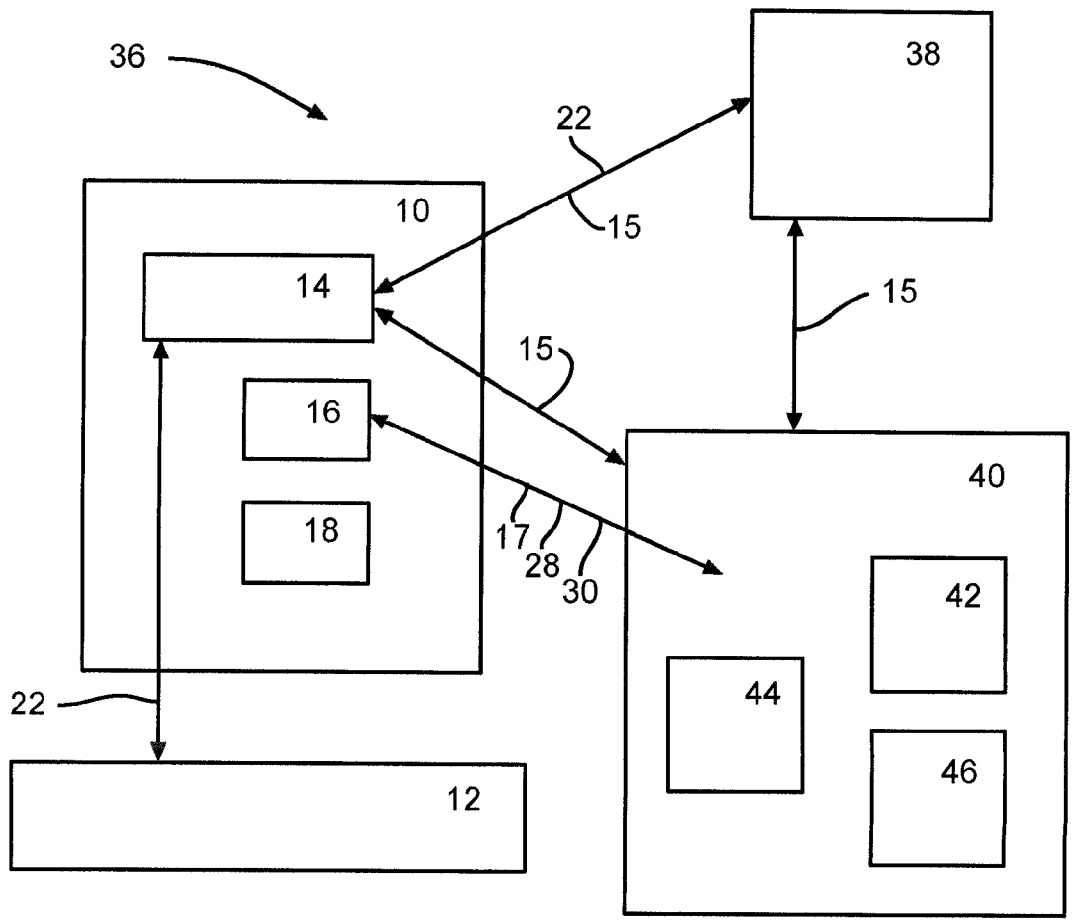
FIG. 4 illustrates a box diagram of one embodiment of an inspection apparatus for non-destructively free-hand inspecting a structure.

FIG. 4 illustrates a box diagram of one embodiment of an inspection apparatus 36 for non-destructively free-hand inspecting the structure 12. The inspection apparatus 36 may comprise the free-hand inspection apparatus 10 of the embodiment of FIGS. 1-3, an inspection device 38, and at least one computer 40. The free-hand inspection apparatus 10 may comprise the array 14, the inertial sensor 16, and the bubble-shoe housing 18 as discussed in FIGS. 1-3. In other embodiments, one or more components of the free-hand inspection apparatus 10 may vary. As shown in FIGS. 1-3, the array 14 may be disposed within the cavity 34 of the bubble-shoe housing 18 which may supply couplant 32 to the surface of the structure 12 being inspected. The inertial sensor 16 may be attached to the bubble-shoe housing 18.

The inspection device 38 may transmit and receive inspection signals 22 to the array 14. The inspection device 38 may comprise an ultrasonic signal device, an eddy current device, a magnetic signal device, and/or another type of inspection device. As shown in FIGS. 1-3, the array 14 may comprise a plurality of elements 20 which may be transducers in a linear array. The array 14 may receive the inspection signals 22 of the inspection device 38. The array 14 may transmit the inspection signals 22 received from the inspection device 38 towards the structure 12 being inspected. The array 14 may receive the inspection signals 22 back from the structure 12 being inspected after the inspection signals 22 have been reflected. The array 14 may transmit the inspection signals 22 received back from the structure 12 to at least one of the inspection device 38 and the at least one computer 40. The free-hand inspection apparatus 10, the inspection device 38, and the at least one computer 40 may each be in communication.

As shown in FIGS. 1-3, the inertial sensor 16 may comprise a micro-electro-mechanical system inertial sensor (MEMS inertial sensor) comprising an accelerometer 24 and a rate gyroscope 26. The inertial sensor 16 may measure acceleration 28 and angular rotation rate 30 data 17 in X, Y, and Z directions of the array 14 relative to the surface of the structure 12 being inspected. The at least one computer 40 may collect and analyze data 15 and 17 from the array 14 and the inertial sensor 16. The at least one computer 40 may determine velocities, positions, and orientations of the array 14 relative to the surface of the structure 12 based on the inertial sensor data 17. The at least one computer 40 may correlate the array data 15 relative to the determined positions of the array 14. The at least one computer 40 may include a controller 42, a clock 44, and/or another type of device for correlating the array data 15 relative to the determined positions and orientations of the array 14. The at least one computer 40 may output inspection results at multiple locations of the surface of the structure 12 based on the correlated array data 15 relative to the determined positions and orientations of the array 14. The at least one computer 40 may include a display 46 for displaying the outputted inspection results of the multiple locations of the surface of the structure 12.

Figure 5:
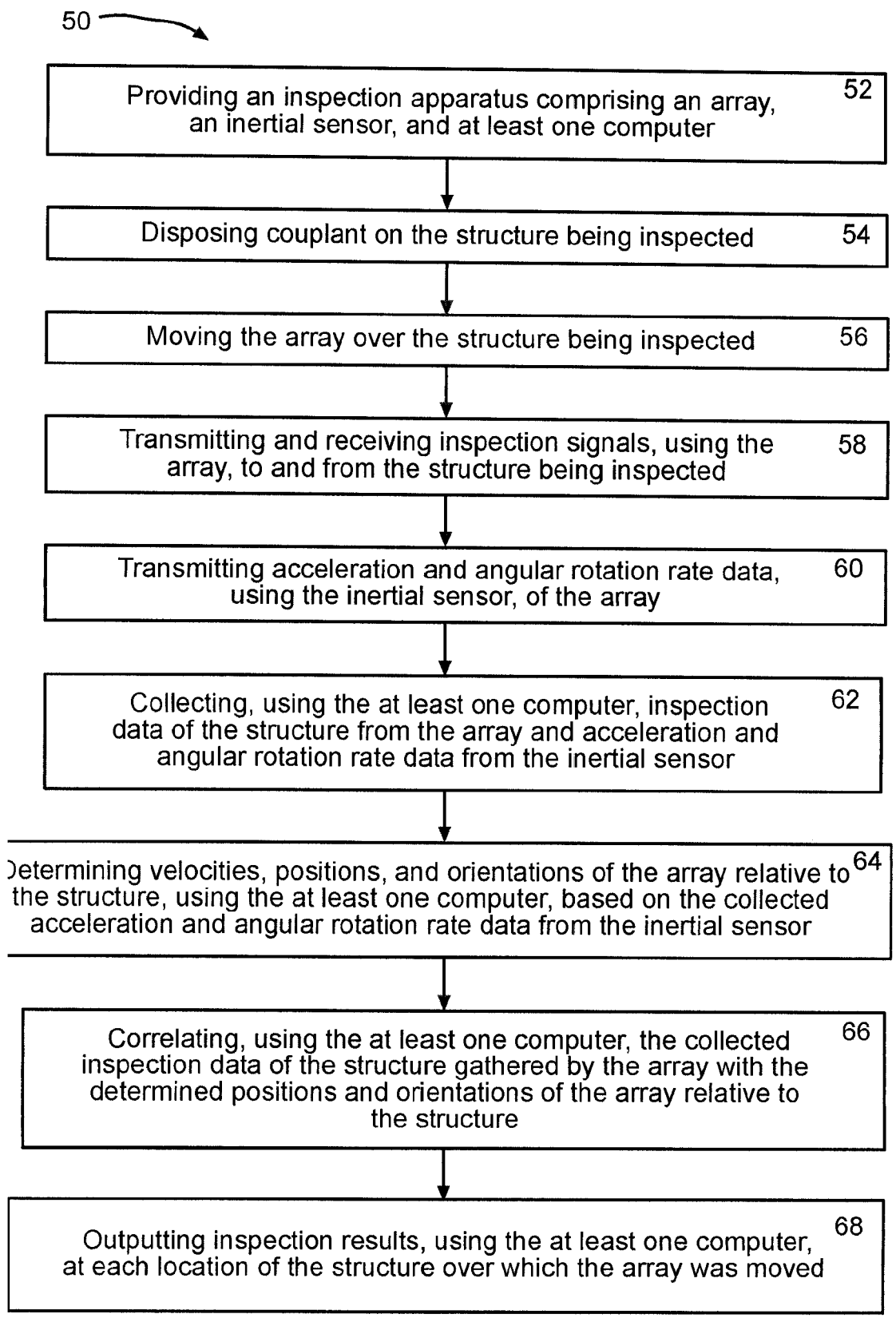
FIG. 5 illustrates a flowchart of one embodiment of a method of non-destructively free-hand inspecting a structure.

FIG. 5 illustrates a flowchart of one embodiment of a method 50 of non-destructively free-hand inspecting a structure 12. The structure 12 may comprise an in-service aircraft, production aircraft, boat hull, automobile, pipe, building, bridge, or another type of structure which needs to be inspected to identify any inconsistencies in the structure. The structure 12 may comprise a linear structure, a three-dimensional curved structure, such as a partial cone or hemisphere, or other type of structure. In step 52, an inspection apparatus 10 may be provided. The provided inspection apparatus 10 may comprise an array 14 comprising a plurality of elements 20, an inertial sensor 16, and at least one computer 40. The array 14 may comprise a linear array, and the elements 20 may comprise transducers. The provided inspection apparatus 10 may further comprise a bubble-shoe housing 18. The array 14 may be disposed within a cavity 34 of the bubble-shoe housing 18 and the inertial sensor 16 may be attached to the bubble-shoe housing 18. The inertial sensor 16 may comprise a micro-electro-mechanical system inertial sensor comprising an accelerometer 28 and a rate gyroscope 26. In other embodiments, the provided inspection apparatus 10, including any of its components, may disclose any of the embodiments disclosed herein. In still other embodiments, the provided inspection apparatus 10 may vary.

In step 54, couplant 32 may be disposed on the surface of the structure using the bubble-shoe housing 18. In step 56, the array 14 may be moved over the surface of the structure 12. As shown in the perspective view of FIG. 6, step 56 may comprise an operator 55 manually sweeping the array 14 over the surface 12 in a pattern 57 in order to inspect the entire structure 12. The operator 55 may manually sweep the array over a structure 12 comprising a linear structure, a three-dimensional curved structure, such as a partial cone or hemisphere, or other type of structure. The structure 12 may have inconsistencies 72 that are on or below the surface of the structure. In step 58, inspection signals 22 may be transmitted and received, using the array 14, to and from the structure 12. The inspection signals 22 may comprise ultrasonic signals, eddy current signals, magnetic signals, and/or other types of inspection signals. The array 14 may gather A-scan data, B-scan data, C-scan data, or other types of data regarding the structure 12.

In step 60, acceleration 28 and angular rotation rate 30 data 17 of the array 14 in X, Y, and Z directions may be transmitted, using the inertial sensor 16. In step 62, inspection data 15 of the structure 12 from the array 14 and acceleration 28 and angular rotation rate 30 data 17 from the inertial sensor 16 may be collected using the at least one computer 40. In step 64, velocities, positions, and orientations of the array 14 relative to the surface of the structure 12 may be determined, using the at least one computer 40, based on the collected acceleration 28 and angular rotation rate 30 data from the inertial sensor 16. Step 64 may comprise the at least one computer 40 using a position algorithm to determine the positions and orientations of the array 14 based on the collected acceleration 28 and angular rotation rate 30 data.

In step 66, the collected inspection data of the structure 12 gathered by the array 14 may be correlated, using the at least one computer 40, with the determined positions and orientations of the array 14 relative to the surface of the structure 12. Step 66 may comprise the at least one computer 40 using a correlation algorithm to correlate the collected inspection data of the structure 12 to the determined positions and orientations of the array 14 relative to the surface of the structure 12. Step 66 may comprise the at least one computer 40 using a controller 42, a clock 44, and/or another type of device for correlating the collected inspection data of the structure 12 gathered by the array 14 relative to the determined positions and orientations of the array 14.

Figure 6:
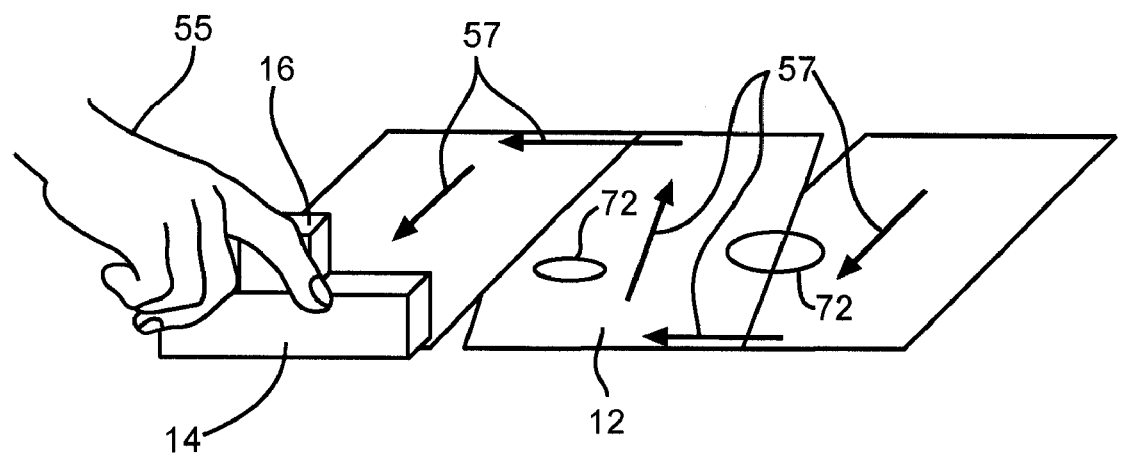
FIG. 6 illustrates a perspective view of an operator manually sweeping the free-hand inspection apparatus of FIG. 1 over a surface of a structure.
Figure 7:
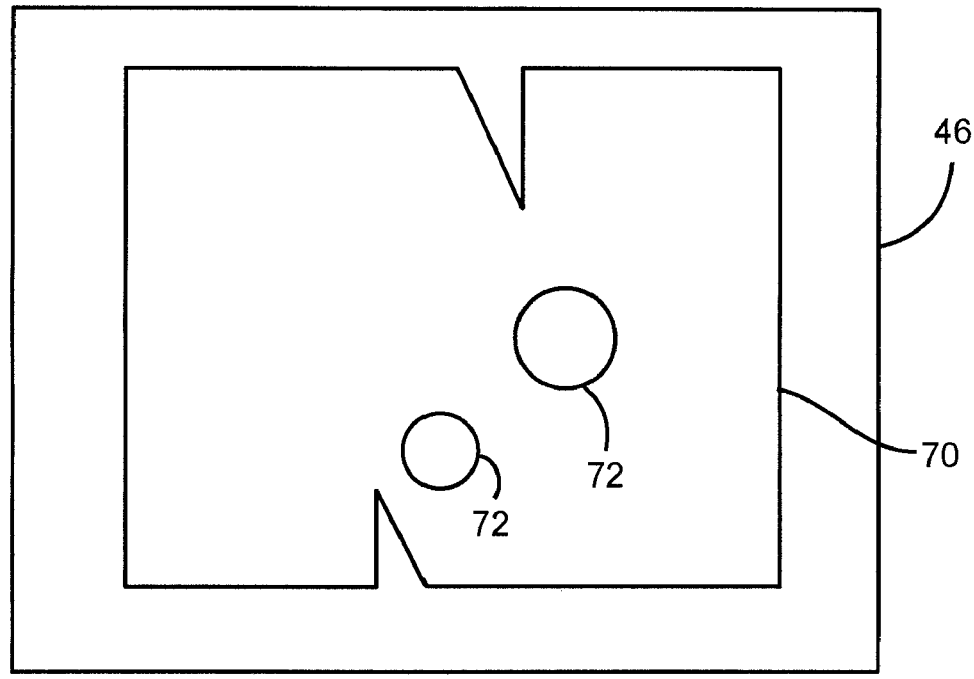
FIG. 7 illustrates a front view of a display image showing inconsistencies in a structure which was inspected by the free-hand inspection apparatus of FIG. 1.

In step 68, inspection results at each location of the surface of the structure 12 over which the array 14 was moved may be outputted using the at least one computer 40. As shown in the perspective view of FIG. 7, step 68 may comprise outputting on a display 46 an image 70 of the interior and/or exterior of the structure 12 of FIG. 6 showing the locations of the surface of the structure 12 over which the array 14 was moved with the image 70 showing the positions of any inconsistencies 72 in the locations of the structure 12. The image 70 may be displayed as an A-Scan format, a B-Scan format, a C-Scan format, or in another type of format. The image 70 may comprise a two-dimensional or a three-dimensional image. Inconsistencies 72 in two or three dimensions may be identified in a linear structure, a three-dimensional curved structure, such as a partial cone or hemisphere, or other type of structure. In such manner, any inconsistencies 72 in the structure 12 may be located, identified, and repaired. In other embodiments, one or more steps of the method 50 may be deleted, modified, or done in another order. In still other embodiments, additional steps may be added to the method 50.

One or more embodiments of the disclosure may allow for rapid free-hand two-dimensional, A-scan, B-scan, or C-scan images of non-destructive data to be taken of three-dimensional structures in order to provide rapid, low cost inconsistency assessment. One or more embodiments of the disclosure may be faster and/or more versatile than one or more of the conventional hand-held scanning non-destructive inspection devices. One or more embodiments of the disclosure may be less expensive than one or more of the conventional automated scanners and phased array UT systems. Due to the use of the array 14 and the inertial sensor 26, the surface 12 may be 'painted' allowing wide swaths of data to be collected free-hand without the necessity of bridge mounting or excessive repetitive motion. Moreover, the operator may not need to take the time and effort required to mount a scanning guide or bridge. Additionally, the true three-dimensional nature of the position of the data taken may allow the data to be projected onto a three-dimensional CAD image of the scanned structure. One or more embodiments of the disclosure may further reduce or eliminate other types of problems experienced with one or more of the conventional non-destructive inspection apparatus and/or methods.

It should be understood, of course, that the foregoing relates to exemplary embodiments of the disclosure and that modifications may be made without departing from the spirit and scope of the disclosure as set forth in the following claims.

We claim:

1. A free-hand inspection apparatus for non-destructively inspecting a structure comprising:
   an array comprising a plurality of elements for transmitting and receiving inspection signals towards and from a structure being inspected; and
   an inertial sensor for measuring acceleration and angular rotation rate in X, Y, and Z directions of the array.

2. The free-hand inspection apparatus of claim 1 wherein the elements comprise transducers.

3. The free-hand inspection apparatus of claim 1 wherein the elements are for transmitting and receiving at least one of ultrasonic signals, eddy current signals, or magnetic signals.

4. The free-hand inspection apparatus of claim 1 wherein the array is a linear array.

5. The free-hand inspection apparatus of claim 1 further comprising a bubble-shoe housing attached to the array for supplying couplant to a surface of a structure being inspected.

6. The free-hand inspection apparatus of claim 5 wherein the array is disposed within a cavity of the bubble-shoe housing and the inertial sensor is attached to the bubble-shoe housing.

7. The free-hand inspection apparatus of claim 1 wherein the inertial sensor comprises a micro-electro-mechanical system inertial sensor comprising an accelerometer and a rate gyroscope.

8. An inspection apparatus for non-destructively free-hand inspecting a structure comprising:
   an inspection device for transmitting and receiving inspection signals;
   an array comprising a plurality of elements for receiving the inspection signals of the inspection device, for transmitting the inspection signals received from the inspection device towards a structure being inspected, and for receiving the inspection signals back from the structure being inspected;
   an inertial sensor for measuring acceleration and angular rotation rate in X, Y, and Z directions of the array relative to a surface of the structure being inspected; and
   at least one computer for collecting and analyzing data from the array and the inertial sensor, for determining velocities, positions, and orientations of the array relative to the surface of the structure based on the inertial sensor data, for correlating the array data relative to the determined positions and orientations of the array, and for outputting inspection results at multiple locations of the structure based on the correlated array data relative to the determined positions and orientations of the array.

9. The inspection apparatus of claim 8 wherein the inspection device comprises at least one of an ultrasonic signal device, an eddy current signal device, or a magnetic signal device.

10. The inspection apparatus of claim 8 wherein the elements comprise transducers.

11. The inspection apparatus of claim 8 wherein the array is a linear array.

12. The inspection apparatus of claim 8 further comprising a bubble-shoe housing for supplying couplant to the surface of the structure being inspected, the array being disposed within a cavity of the bubble-shoe housing and the inertial sensor being attached to the bubble-shoe housing.

13. The inspection apparatus of claim 8 wherein the inertial sensor comprises a micro-electro-mechanical system inertial sensor comprising an accelerometer and a rate gyroscope.

14. The inspection apparatus of claim 8 wherein the at least one computer further comprises at least one of a controller or a clock for correlating the array data relative to the determined positions and orientations of the array.

15. The inspection apparatus of claim 8 wherein the at least one computer further comprises a display for displaying the outputted inspection results of the multiple locations of the structure.

16. A method of non-destructively free-hand inspecting a structure comprising:
- providing an inspection apparatus comprising an array comprising a plurality of elements, an inertial sensor, and at least one computer;
- moving the array over a surface of the structure;
- using the array to transmit and receive inspection signals to and from the structure;
- using the inertial sensor to transmit acceleration and angular rotation rate data of the array in X, Y, and Z directions;
- using the at least one computer to collect inspection data of the structure from the array and the acceleration and angular rotation rate data from the inertial sensor;
- using the at least one computer to determine velocities, positions, and orientations of the array relative to the surface of the structure based on the collected acceleration and angular rotation rate data from the inertial sensor;
- using the at least one computer to correlate the collected inspection data of the structure with the determined positions and orientations of the array relative to the surface; and
- using the at least one computer to output inspection results at each location of the surface of the structure over which the array was moved.

17. The method of claim 16 wherein the structure comprises a structure of an in-service aircraft.

18. The method of claim 16 wherein at least one of the array comprises a linear array, or the elements comprise transducers.

19. The method of claim 16 wherein the provided inspection apparatus further comprises a bubble-shoe housing, wherein the array is disposed within a cavity of the bubble shoe housing and the inertial sensor is attached to the bubble-shoe housing, and further comprising the step of using the bubble-shoe housing to dispose couplant on the surface of the structure.

20. The method of claim 16 wherein the inspection signals comprise at least one of ultrasonic signals, eddy current signals, or magnetic signals.

21. The method of claim 16 wherein the inertial sensor comprises a micro-electro-mechanical system inertial sensor comprising an accelerometer and a rate gyroscope.

22. The method of claim 16 wherein the moving step comprises an operator manually sweeping the array over the surface of the structure in a pattern.

23. The method of claim 16 wherein the using the at least one computer to determine step comprises the at least one computer using a position algorithm to determine the positions and orientations of the array based on the collected acceleration and angular rotation rate data.

24. The method of claim 16 wherein the using the at least one computer to correlate step comprises the at least one computer using a correlation algorithm to correlate the collected inspection data of the structure to the determined positions and orientations of the array relative to the surface of the structure.

25. The method of claim 16 wherein the using the at least one computer to output step comprises the at least one computer outputting on a display an image of the structure showing the locations of the surface of the structure over which the array was moved with the image showing positions of any inconsistencies in the locations of the structure.

26. A free-hand inspection apparatus for non-destructively inspecting a structure comprising:
- an array comprising a plurality of elements for transmitting and receiving inspection signals towards and from a structure being inspected;
- an inertial sensor for measuring acceleration and angular rotation rate in X, Y, and Z directions of the array relative to a surface of a structure being inspected; and
- at least one computer for collecting and analyzing data from the array and the inertial sensor, for determining velocities, positions, and orientations of the array relative to a surface of a structure based on the inertial sensor data, for correlating the array data relative to the determined positions and orientations of the array, and for outputting inspection results at multiple locations of a structure based on the correlated array data relative to the determined positions and orientations of the array.

* * * * *